United States Patent [19]
Yoshida et al.

[11] Patent Number: 5,973,214
[45] Date of Patent: Oct. 26, 1999

[54] METHOD FOR PRODUCING AN OPTICALLY ACTIVE 2-ALKANOL

[75] Inventors: Naoyuki Yoshida; Hitoshi Yano, both of Ichihara, Japan

[73] Assignee: Chisso Corporation, Osaka, Japan

[21] Appl. No.: 09/154,247

[22] Filed: Sep. 16, 1998

[30] Foreign Application Priority Data

Sep. 25, 1997 [JP] Japan .................................. 9-278210

[51] Int. Cl.$^6$ .................................................. C07C 29/03
[52] U.S. Cl. ......................... 568/902; 568/840; 568/844; 560/231; 560/234
[58] Field of Search .................................. 568/902, 840, 568/844; 560/231, 234

[56] References Cited

PUBLICATIONS

CA 111: 95626 Optically active 1–halogen–2–alkanol derivatives and their enzymic manufacture. Hamaguchi et al, 1987.

CA 124: 115594 Process for producing optically active propargyl alcohol compound. Kameo et al, 1995.

CA 124: 86035 Lipase–catalyzed . . . acylation. Naemurz et al, 1995.

*Primary Examiner*—Joseph K. McKane
*Attorney, Agent, or Firm*—Browdy and Neimark

[57] ABSTRACT

Both enantiomers of optically active 2-alkanol are produced by transesterification reaction of racemic 2-alkanol and aliphatic acid 2,2,2-trichloroethylester in the presence of enzyme derived from *Candida antarctica*.

Both enantiomers of optically active 2-alkanol, which are useful as starting materials of liquid crystal materials and have optical purity of 99% or more, can be efficiently produced.

4 Claims, No Drawings

METHOD FOR PRODUCING AN OPTICALLY ACTIVE 2-ALKANOL

TECHNICAL FIELD

The present invention relates to a method for producing an optically active 2-alkanol useful for a chiral building block, which is added to a liquid crystal composition, and useful for raw materials of ferroelectric liquid crystal compounds.

BACKGROUND OF THE ART

As a method for producing an optically active 2-alkanol, several methods, such as an optical resolution method of an ester exchange reaction using enzyme or an optical resolution method using hydrolysis, are known. Specifically, many methods reported in recent years are those for producing compounds having optical purity of more than 90% ee. However, in almost methods, only one of both enantiomers has good purity, but the other has optical purity of less than 80% ee (for example, Tetrahedron Lett., 1995, 36, 6663; Biotechnol. Lett., 1992, 15, 2159).

Further, there are some methods for producing both enantiomers having optical purity of more than 90% ee (for example, Tetrahedron Asymm., 1995, 6, 1217; Tetrahedron Lett., 1993, 34, 1367; Japanese Patent Laid-open Publication No. 6-169794). However, in the stereoselectivity, both enantiomers having optical purity of more than 99% ee are unknown.

In optical active 2-alkanol as liquid crystal materials, both enantiomers are necessary, and each optical purity of 99 % ee or more is required. For this reason, hitherto, it has been conducted to use insufficient methods such as recrystallization after leading the compound obtained by optical resolution to its derivative, or repeated enzyme reaction, to provide compounds having optical purity of more than 99% ee.

There are transesterification reactions using the enzyme derived from *Candida antarctica* (microbiotics) (Tetrahedron Lett., 36(37), 6663-4), or using aliphatic acid trichloroethyl ester (Japanese Patent Publication No. 06-104661). In general, stereoselectivity of the transesterification reaction using an enzyme is influenced by the combination of alcohol, which is a substrate, ester, which is an acylating agent, and the enzyme, so that the suitability is unknown until the reaction is conducted. In all of the said methods, the optical purity is no more than 90% ee.

Accordingly, a simple method for producing optical active 2-alkanol having both enantiomers showing optical purity of more than 99% ee has been desired.

DISCLOSURE OF INVENTION

The present inventors earnestly studied a method for efficiently producing optically active 2-alkanol having both enantiomers showing optical purity of more than 99% ee to solve the said problems, and the present invention has been completed by finding a method for producing optically active pure 2-alkanol and aliphatic acid 2-alkyl ester, comprising proceeding an ester exchange reaction in the presence of the enzyme derived from *Candida antarctica* in a mixture of 2-alkanol represented by general formula (1):

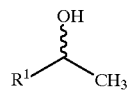

wherein $R^1$ indicates straight or branched alkyl of 3–20 carbons, and aliphatic acid trichloroethylester represented by general formula (2):

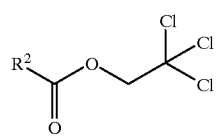

wherein $R^2$ indicates straight or branched alkyl of 1–30 carbons.

The combination of alcohol, an acylating agent and enzyme shown in this production method has not been known, and it has been found by the present inventors.

The present invention is represented by the following reaction formula.

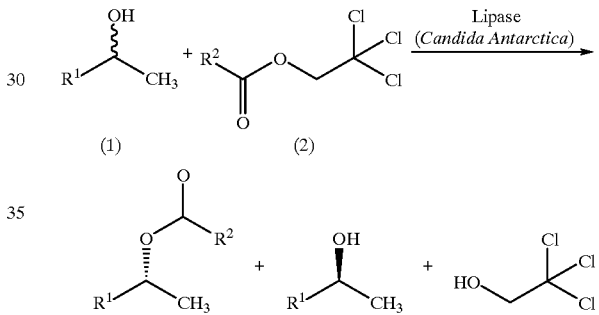

Many of 2-Alkanol (1) of the starting material are on the market and can be easily obtained. Aliphatic acid trichloroethyl ester (2) of the other starting material can be obtained by common esterification methods, such as dehydration and condensation of easily available aliphatic acid and 2,2,2-trichloroethanol in the presence of an acid catalyst, or a reaction of 2,2,2-trichloro ethanol in the presence of a base such as triethyl amine with aliphatic acid chloride, which is obtained by treating an aliphatic acid with thionyl chloride. Aliphatic acid having 2–31 carbon atoms, preferably caproic acid having 6 carbons, can be used.

As the enzyme derived from *Candida antarctica,* the enzyme having the ability of ester exchange such as lipase or esterase can be generally used. The form of enzyme is not limited, for example, extract or solid can be used. Products of Novo Nordisk Co., Ltd., such as Novozyme 435 or Chirazyme available from Boehlinger Mannheim K.K., can be preferably used.

Compound (1) and compound (2) are mixed at a molar ratio of 1/1-2/1, preferably 2/1, and the enzyme of 0.1–10% by weight to compound (1), preferably 1–2% by weight, which is derived from *Candida antarctica,* is added with stirring to the mixture at a temperature of 35° C.–40° C.

After reacting the mixture for desired hours, for example 1–48 hours, preferably 4–8 hours, the conversion of 50% or more is confirmed by gas chromatography and the like, and the stirring is stopped. The enzyme can be removed by filtering. The filtrate is distilled off under reduced pressure to obtain 2,2,2-trichloroethanol, (S)-2-alkanol and (R)-2-alkylester.

2,2,2-Trichloroethanol can be reused by esterification of aliphatic acid for transesterification reaction. (R)-2-alkylester can be changed to (R)-2-alkanol by chemical hydrolysis operation.

BEST MODE FOR CARRYING OUT THE INVENTION

The following examples are intended to further illustrate the present invention and not to limit the invention by these examples.

EXAMPLE 1

Step 1

Racemic 2-octanol 13.0 g (0.1 mol), 2,2,2-trichloroethyl caproate 12.4 g (0.05 mol) and enzyme (Novozyme 435, manufactured by Novo Nordisk Co., Ltd.) 0.2 g were mixed, and the mixture was stirred for 23 hours at 40° C. The reactant was filtered off. The enzyme on the filter was washed with heptane 20 ml. The filtrate was concentrated under reduced pressure. The residue was purified by distillation under reduced pressure. 2,2,2-Trichloroethanol, and then S-(+)-2-octanol were separated by distillation. Lastly, the main R-(−)-2-octyl caproate 9.96 g (boiling point: 99–101° C./3 mmHg) was obtained.

Step 2

R-(−)-2-octyl caproate 9.96 g (0.0438 mol), an aqueous solution (22 ml) of sodium hydroxide 1.8 g (0.045 mol) and ethanol 2 ml were mixed, and the mixture was heated and refluxed. After the disappearance of ester was confirmed by gas chromatography, the reactant was cooled to room temperature, extracted with chloroform (total 100 ml) and dried over anhydrous magnesium sulfate. After magnesium sulfate was filtered off, the solution was concentrated under reduced pressure to obtain R-(−)-2-octanol 5.2 g (0.0398 mol).

3,5-Dinitrophenylisocyanate 40 mg (0.192 mmol) was added to R-(−)-2-octanol 25 mg (0.192 mmol), the mixture was heated for one hour at 60° C. and diluted with chloroform 3 ml, and undissolved materials were filtered off.

The filtrate 5 ml was analyzed by HPLC (SUMICHIRAL OA-3000), and the optical purity was 99.8% ee.

In the same manner, the said S-(+)-2-octanol was analyzed, and the optical purity was 99.7% ee.

By using the production method of the present invention, both enantiomers of 2-alkanol having optical purity of 99% ee or more are efficiently obtained, respectively. 2-Alkanol having optically high purity can be used as starting materials of liquid crystal materials.

We claim:

1. A method for producing an optically active 2-alkanol comprising conducting a transesterification reaction by using a mixture of 2-alkanol represented by general formula (1):

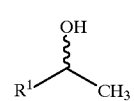

(1)

wherein $R^1$ indicates straight or branched alkyl of 3–20 carbon atoms, and aliphatic acid trichloroethylester represented by general formula (2),

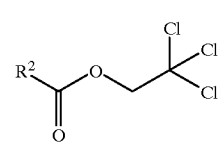

(2)

wherein $R^2$ indicates straight or branched alkyl of 1–30 carbon atoms, in the presence of an enzyme derived from *Candida antarctica*, and obtaining an optically pure 2-alkanol and aliphatic acid 2-alkylester.

2. A method for producing an optically active 2-alkanol claimed in claim 1, wherein $R^2$ is pentyl in general formula (2).

3. A method for producing an optically active 2-alkanol claimed in claim 1, wherein $R^1$ is hexyl in general formula (1).

4. A method for producing an optically active 2-alkanol claimed in claim 1, wherein $R^1$ is hexyl in general formula (1) and $R^2$ is pentyl in general formula (2).

* * * * *